United States Patent [19]

La Tour

[11] Patent Number: 4,634,436

[45] Date of Patent: Jan. 6, 1987

[54] METHOD FOR MAKING A BODY WRAP COMPOSITION

[76] Inventor: June T. La Tour, 2619 Palms Rd., Richmond, Mich. 48062

[21] Appl. No.: 510,658

[22] Filed: Jul. 5, 1983

[51] Int. Cl.⁴ .................... A61M 35/00; A61F 13/00
[52] U.S. Cl. ...................................... 604/290; 424/28; 424/195.1; 604/289; 604/303; 604/304; 604/308; 514/786
[58] Field of Search ............... 604/289, 290, 303, 304, 604/308; 424/364, 28, 358; 128/261

[56] References Cited

U.S. PATENT DOCUMENTS

| | | | |
|---|---|---|---|
| 3,150,049 | 9/1964 | Emory | 167/90 |
| 3,810,996 | 5/1974 | Sutliff et al. | 424/364 |
| 3,896,807 | 7/1975 | Buchalter | 128/261 |
| 3,939,260 | 2/1976 | Lafon | 424/28 |
| 4,238,509 | 12/1980 | Evans et al. | 424/358 |

Primary Examiner—Herbert S. Cockeram
Attorney, Agent, or Firm—Russel C. Wells

[57] ABSTRACT

A composition and body wrap comprising several herbs forms the basis for a solution, salve and an oil which is applied to the body. The body is completely wrapped and covered with a non-porous membrane to retain the body heat. The method of making the solution, salve and oil is described using nutrients such as lecithin, herbs such as kelp, parsley, chickweed, and, alfalfa, and sesame oil and water. A carrier used to keep the solution on the body is a foam or sponge material and the non-porous membrane is a thin plastic material. All of the materials are disposed of after one use.

3 Claims, No Drawings

METHOD FOR MAKING A BODY WRAP COMPOSITION

This invention relates to compositions in general and to herbal compositions for use on human bodies in particular.

DESCRIPTION OF PRIOR ART

In U.S. Pat. No. 416,730 issued to Hilke and entitled "Liniment" there is described a liniment for burns comprising chaulk, flaxseed-oil, vinegar and chamomile infusion which when mixed together was added to a covering and placed over the affected area on the body. This patent teaches the use of some natural products in a medicine which is applied in a covered manner.

In U.S. Pat. No. 3,150,049 issued to Emory and entitled "Bath Oil" there is described an oil which is applied to the body after cleansing. This teaches the combination of lecithin and a perfume oil in other materials. The purpose of the perfume oil is to make the scent of the oil bearable to the user.

In U.S. Pat. No. 3,810,996 issued to Sutliff et al. entitled "Cosmetic Preparation" teaches a facial mask composition which hardens on the skin.

In U.S. Pat. No. 3,896,807 issued to Buchalter entitled "Article Impregnated with Skin-Care Formulations" illustrates the use of an article of apparel as a covering for carrying a therapeutic substance to a small area of the skin.

In U.S. Pat. No. 3,939,260 issued to Lafon entitled "Therapeutic and Cosmetic Compositions" teaches a cream to be used on the skin containing lyophillesed oil-in-water emulsions and suspensions.

In U.S. Pat. No. 4,238,509 issued to Evans et al. there is taught the use of oat flour mixed with an oil gel to reduce the greasiness associated with the oil gel. The use is in cosmetics.

In the above identified patents, only Sutliff et al., Emory, Evans et al., and Hilke disclose one of the ingredients of the present invention. In each instance, following their teachings, the oil, salve and solution of the present invention will not be arrived at.

SUMMARY OF THE INVENTION

The invention herein is a method of preparing and applying to the human body an oil, salve and solution for the purpose of inducing into the body several natural nutrients. The solution is a mixture of lecithin, kelp, parsley, and alfalfa and/or chickweed. The solution is mixed together in water and brought to a boil. The temperature is then reduced for a period of time of two hours and then the temperature is removed and the solution is cooled for approximately one hour.

The liquid is poured off and the residue is then mixed with granulated lecithin and an oil formed of sesame oil and liquid lecithin forming a salve. These three compositions, the oil, salve and the liquid are then applied in steps to the human body for the purpose of feeding the natural nutrients carried by the ingredients into the body.

The steps of application are to cover the body with the oil. Next the salve is applied to those parts of the body which contain some affected symptoms. This is typically an area that is sprained, maybe has some arthritic pain, or any general discomfort. Lastly the whole body is wrapped in a material such as foam which has been soaked in the liquid. After wrapping, the body is covered for an hour by a thin membrane which retains all of the body heat. The result is soothing temporary relief from the affliction.

DETAILED DESCRIPTION

The human body generates and utilizes many nutrients. These nutrients are used to balance the body functions and healing processes so that the body can effectively ward off discomfort and to some extent pain. Many other uses of these nutrients include providing and storing energy, building nerve, brain, heat, and liver tissues; emulsifying fats and cholesterol; "burning" and distributing fats; sustaining healthy hearts and blood vessels; distributing and conserving oxygen; and supporting vitality and sex functions. In addition it has been found that oil-based nutrients seem to act with vitamins B and C as safeguards against degenerative diseases of the heart, liver, kidney, blood and brain, and against senility.

The composition for the human body is prepared using several natural nutrients, each selected to provide additional body food for use by the body to comfort an affected area.

The first nutrient is granulated lecithin. It has been found that lecithin is not needed as a food supplement in that it is found in sufficient amounts in the body when supplied by normal diets. The purpose of lecithin is to act as an emulsifier and agent for distributing and using fats in the human body. Natural sources for lecithin are most raw vegetable seed oils, such as those of corn, wheat germ, safflower, soy, sunflower, pumpkin and sesame.

The next ingredient is kelp or seaweed. An analysis of seaweed by the Norwegian Seaweed Institute as reported in "Review of Seaweed Research", Research Series No. 76, Clemson University, 1966, shows that seaweed contains at least 60 interacting nutrients and 8 vitamins. Primarily it is known for its trace minerals and in particular iodine which is needed by the thyroid gland.

Parsley powder is used as a diuretic to relieve the distress of uric acid concretions by a solvent or flushing action. Many other herbs could be used such as juniper berry, gravel root, uva ursi, etc.

Alfalfa and/or chickweed powder is used to soothe arthritic and rheumatic pain. They are rich in vitamin A, B6, E, and K. In addition alfalfa is a high protein content herb.

The herbal solution is formed from the above identified ingredients in the following proportions:
  3 parts by volume of each of the following powders: kelp, parsley, and alfalfa and/or chickweed;
  6 parts by volume of granulated lecithin; and
  64 parts by volume of water.

This mixture is heated to a boiling point, but is not allowed to boil. This is a temperature of 100 degrees centigrade or 212 degrees fahrenheit. Once the boiling point is reached the temperature is reduced to 65 degrees centigrade or 150 degrees fahrenheit for a period of approximately 2 hours. The color of the solution at the end of 2 hours is green-brown. Next the temperature is removed and the solution cools to or below a temperature which is comfortable to the touch. This cooling period is about one hour long.

The liquid is poured off leaving a residue which will become a major ingredient for the salve. Eight parts by volume of the residue is mixed with one part by volume of granulated lecithin and two parts by volume of each of sesame oil and liquid lecithin. This mixture is an herbal salve.

The third composition is an oil which is formed from equal parts of sesame oil and liquid lecithin. Sesame oil has a high stability. It has been found that sesame oil has a unique effectiveness in helping to increase the number of blood platelets in the body.

Liquid lecithin, which typically comes from soybean oil, is used in the body to transport and utilize fats.

The process of using the solution, salve and oil on the human body is by the following steps. First the body is covered by the oil which is applied by spreading. The oil functions as base for holding the nutrients from the salve and the solution for absorption by the body. It is believed that the nutrients from the oil are also absorbed by the body.

The salve is then applied to the affected parts of the body where it is believed the concentrated nutrients will be beneficial. Such affected areas may be sprains, soreness, arthritic and rheumatic pain and other similar symptoms.

The complete body, with the exception of the head, is then wrapped in a carrier which has been soaked in the solution. One such carrier is an extremely thin foam which is disposable after use. The thinness allows the foam to form to the body and the foam itself provides a carrier to retain the solution. Other materials such as flannel, etc. which will retain the solution are acceptable. The carrier is then retained in place by any flexible binder that will not shrink and compress on the body.

After wrapping, the body is then covered by a thin membrane which functions to prevent the evaporation of the solution and body heat loss. The heat of the body assists in the process of absorption of the nutrients. The membrane is kept on the body for a period of time between 60 and 90 minutes. The comfort of the patient is the foremost criterion for determining the length of the time the membrane is on the body.

When the body is completely wrapped and covered by the membrane, the patient is placed in a comfortable reclining position with little movement for the 60 to 90 minutes. At the end of this time the body is completely unwrapped and all the wrapping including the foam, binder, and membrane is disposed of. The patient is towelled dry and resumes his or her activity.

To the solution, I have found that acetic acid in the form of apple cider vinegar is helpful as a cleansing agent. The amount used is much less than any of the other ingredients and is about 3 parts by volume.

In order to make the scent of the solution, salve, and oil more pleasant to the patient, I add a very small amount of essential oil such as natural vanilla. Any perfumed oil will do as its only purpose is to provide a pleasing scent.

There has thus been described a herbal solution, salve and oil and a method of using such solution, salve and oil on the human body for the purpose of providing a soothing and comforting relief to affected areas. This is accomplished by an osmosis feeding from outside the body of certain nutrients to balance out the nutrients within the body and thereby allowing the body to heal itself.

What I claim:

1. A method for making a composition for a body wrap comprising the steps of:
   mixing together in a suitable container the following ingredients,
   6 parts by volume of lecithin;
   3 parts by volume of kelp;
   3 parts by volume of parsley;
   3 parts by volume of alfalfa; and
   64 parts by volume of water;
   bringing the mixture to a temperature having a range between 200 degrees fahrenheit and 212 degrees fahrenheit;
   lowering the temperature to 150 degrees fahrenheit for a time period of two hours;
   removing the source of heat for a time period of one hour; and then
   draining the liquid from the mixture leaving a solid substance.

2. The method according to claim 1 additionally including the step of adding to the initial mixture 3 parts by volume of an apple cider vinegar solution.

3. The method according to claim 2 additionally including the step of adding to the initial mixture 1½ parts by volume of natural vanilla.

* * * * *